United States Patent [19]

Mizuno et al.

[11] Patent Number: Plant 7,023

[45] Date of Patent: Sep. 12, 1989

[54] PEACH TREE, FANCY LADY

[76] Inventors: Walter K. Mizuno; Wallace T. Mizuno, both of 16542 E. Manning, Reedley, Calif. 93654

[21] Appl. No.: 268,345

[22] Filed: Nov. 7, 1988

[51] Int. Cl.[4] ..... A01H 5/00

[52] U.S. Cl. ..... Plt./43

[58] Field of Search ..... Plt./43

*Primary Examiner*—Robert E. Bagwill

*Attorney, Agent, or Firm*—Worrel & Worrel

[57] ABSTRACT

A new and distinct variety of Peach Tree which is denominated varietally as "Fancy Lady" and which is somewhat similar to the Sparkle Peach Treet (U.S. Plant Pat. No. 3,298) with which it is most closely related, the subject variety characterized principally as to novelty by producing fruit which are mature for harvesting and shipment approximately one month earlier than the fruit produced by the Sparkle variety of peach tree in the San Joaquin Valley of central California.

1 Drawing Sheet

BACKGROUND OF THE NEW VARIETY

The present invention relates to a new and novel Peach Tree which has been denominated varietally as "Fancy Lady" and more particularly to a peach tree which produces fruit that have an attractive orange-red skin color and which further ripen for commercial harvesting and shipment approximately the same time of the season as the fruit produced by the Redtop Peach Tree (believed unpatented), and approximately one month earlier than the Sparkle Peach Tree (U.S. Plant Pat. No. 3,298) from which it was derived as a chance mutation. The Peach Tree "Fancy Lady" is further distinguished from the above-identified varieties and characterized principally as to novelty by bearing fruit which are more highly colored than that produced by the Redtop variety of peach tree and which further produces fruit which have a much more distinctive and symmetrical shape than that produced by the Sparkle variety of peach tree, the fruit of the instant variety having a balanced and pleasant flavor as well as noteworthy storage characteristics.

The Sparkle Peach Tree (U.S. Plant Pat. No. 3,298) is well known as a highly productive producer of midseason peaches, the fruit of the Sparkle Peach Tree characterized principally by fruit which may display a very rough, calloused fruit suture and which further characteristically displays an asymmetrical fruit shape. More particularly, the fruit of the Sparkle variety of Peach Tree may appear quite asymmetrical with one-half of the fruit becoming substantially larger than the other half. The fruit of the Sparkle Peach Tree become ripe for harvesting and shipment during the third and fourth week of July in the San Joaquin Valley of central California.

It has long been recognized that it would be desirable to have a peach tree that somewhat remotely resembles the Sparkle variety of Peach Tree (U.S. Plant Pat. No. 3,298) but which is ripe for commercial harvesting and shipment approximately one month earlier than the Sparkle Peach Tree and at approximately the same time of the season as the Redtop Peach Tree (believed unpatented), whereby the demand for such a fruit may be effectively satisfied over a longer period of time. Moreover, the "Fancy Lady" variety of peach tree produces fruit which are more highly colored and more symmetrical in shape than the fruit produced by the Sparkle Peach Tree and further has an attractive orange-red skin color and a balanced and pleasant flavor.

ORIGIN AND ASEXUAL REPRODUCTION OF THE NEW VARIETY

The new and distinct variety of Peach Tree hereof was discovered as a scaffold mutation growing within the cultivated area of the inventors' orchard which is located at 16542 East Manning in Reedley, Fresno County, Calif. in 1976. The scaffold mutation was noted at that time to have desirable characteristics, and the inventors marked the mutation for subsequent evaluation. After observing and evaluating the fruit produced by the mutation over a number of years, the applicants in 1986 directed employees to remove bud wood from the mutation and graft it into several test trees which are located on the same property in Reedley, Calif. The inventors have continually observed the aforementioned test seedlings and have evaluated the fruit produced therefrom and it has been subsequently determined that this first asexual propagation of the instant variety resulted in progeny being produced that possessed the same distinctive characteristics as the original scaffold mutation.

SUMMARY THE NEW VARIETY

The "Fancy Lady" variety of Peach Tree described herein is characterized principally as to novelty by producing fruit which are mature for commercial harvesting and shipment during the third week of June. This date of harvesting is approximately at the same time of the season as the Redtop Peach Tree (believed unpatented) with which it is most closely similar with respect to its date of harvest, but from which it is distinguished by producing fruit which are generally considered to be more highly colored than the fruit produced by the Redtop variety of peach tree and which further has a larger size and a pleasant and well balanced flavor. Further, the new and novel variety "Fancy Lady" is similar in appearance to the Sparkle variety Peach Tree (U.S. Plant Pat. No. 3,298) from which it was discovered as a chance mutation, but which is distinguished therefrom by being ripe for harvesting and shipment approximately one month earlier than the fruit produced by the Sparkle variety Peach Tree.

BRIEF DESCRIPTION OF THE DRAWINGS

The accompanying drawing is a color photograph of five mature fruit of the subject variety, one of which has been divided in the suture plane to show the flesh and stone characteristics, together with a twig bearing typical leaves showing the characteristic coloration thereof, all of the subject variety.

DETAILED DESCRIPTION

Referring more specifically to the pomological details of this new and distinct variety of peach tree, the following has been observed under the ecological conditions prevailing at the orchard of the inventor which is located at 16542 East Manning in Reedley, Fresno County, Calif. All major color code designations are by reference to the Dictionary of Color, by Maerz and Paul, Second Edition, 1950. Common color names are also employed occasionally.

TREE

Size:

*Generally.*—Medium to large depending upon pruning practices.

Vigor: Vigorous and hardy when grown under typical San Joaquin Valley ecological conditions.

Figure: Upright and occasionally upright spreading; the eventual form of the tree may be modified somewhat by pruning practices.

Productivity: Very productive.

Regularity of bearing: Regular.

Trunk:

*Size.*—Generally — Average.

*Bark.*—Surface Texture — Average for the particular species. Color — Grayish although having a slight brown tint (7-C-7).

*Lenticels.*—Generally — Numerous large bark lenticels are evident. Calloused tissue generally surrounds the lenticel openings.

*Calloused tissue.*—Color — Brown, (6-C-9).

Branches:

*Size.*—Generally — Average.

*Surface texture.*—Normal for the species.

*Color.*—Wood which is greater than one year old assumes a brown color, (7-A-10). Current season growth assumes a light green color, (17-H-6). Further, the current season growth may often be tinged with red in the vicinity of exposed surfaces.

*Surface texture.*—Current season growth — Smooth.

LEAVES

Size:

*Generally.*—Large.

*Average length including the petiole.*—Approximately 19.5 cm.

*Average width.*—Approximately 5.4 cm.

*Leaf form.*—Generally — Strongly lanceolate. The tip of the subject variety is acuminate and is moderately reflexed. Further, the tip usually appears twisted.

Color:

*Upper leaf surface.*—Dark green, (24-L-4).

*Lower leaf surface.*—Grey-green, (23-H-3).

*Mid-vein.*—Size — The mid-vein appears quite large on the lower surface of the leaf and is approximately 1 mm. in thickness when measured at the approximate center thereof. Color — Light green-yellow, (18-I-4).

Leaf margins:

*Form.*—Crenate with large regular crenations. Mature leaves display a slightly undulate leaf margin and young leaves may from time to time display a strongly undulate leaf margin.

Leaf petiole:

*Length.*—Approximately 10–12 mm.

*Thickness.*—Approximately 2 mm.

*Color.*—Light green, (17-J-5). The petiole groove may appear somewhat darker.

Leaf glands:

*Form.*—Variable, the leaf glands can in most instances be characterized as reniform although stalked globose glands may occasionally be found on the petiole.

*Numbers.*—Variable, from four to as many as twelve leaf glands may be found. As a general matter, four glands are located in alternative positions on the leaf petiole and four more glands appear along the basal leaf margin. The glands occurring along the basal leaf margin are nearly always reniform.

*Color.*—Yellow-green, (18-K-4). This color darkens with senescence.

Leaf stipules:

*Numbers.*—Two leaf stipules usually are evident and subtend the leaf petiole.

*Color.*—Light green, (18-J-6).

*Surface texture.*—Smooth and shiny.

*Stipule margins.*—Serrate. Reddish colored trichomes may also be evident along the stipule margins. The stipule color darkens with senescence. The leaf stipules are considered to be early deciduous.

*Average length.*—Approximately 10–12 mm.

FLOWERS

Date of bloom: Approximately February 27, in Reedley, Calif. The date of bloom is considered to be mid-season and perhaps somewhat slightly early in relation to other peach cultivars which are growing in the San Joaquin Valley of central California. The date of bloom is approximately three to four days prior to the date of bloom for the Sparkle variety peach tree (U.S. Plant Pat. No. 3,298).

Flower size:

*Generally.*—Small and nonshowy. The size of the flower is considered to be average for this particular bloom type.

*Diameter when fully expanded.*—Approximately 20–21 mm.

*Bloom.*—Generally — The bloom is considered abundant and similar in characteristics to the Sparkle variety of peach tree.

*Bud scales.*—Color — Grey-brown, (7-C-9). Texture — Pubescent.

*Flower buds.*—Size — Average. Shape — Conic.

*Flower production.*—Generally — The variety most commonly produces one flower per node.

*Flower petals.*—Size — Small.

*Average length.*—Approximately 11–12 mm.

*Average width.*—Approximately 8–9 mm.

*Claw.*—Form — Tapering and truncate. The petals are often rolled inwardly and have a moderately undulate margin.

*Petal color.*—Light pink in the median areas, (2-C-2). The petals may also have a darker rose color edge or margin (2-G-2).

*Pedicel.*—Length — Short, approximately 2.5 to 3 mm. Average Thickness — Approximately 1 mm. Color — Green, (20-J-4).

*Nectaries.*—Color — Orange, (11-I-11). The color darkens with advancing maturity.

*Anthers.*—Size — Average for the species. Dorsal Color — Red, (5-K-9). Ventral Color — Buff, (9-J-4).

*Pollen production.*—Generally — Abundant.

*Pollen color — Yellow,* (10-L-3).

*Stamens.*—Average Length — Approximately 12–13 mm. Color — Light Pink when immature, (2-C-1). The stamens turn a dark violet color, (3-J-5) with advancing maturity.

*Pistil and ovary.*—Length — Approximately 12 to 13 mm. The length is somewhat shorter than the fully expanded stamens. Color — Yellow-green, (17-F-2). Surface texture — Pubescent. Further, the ovary may appear somewhat more greenish, (17-G-3). The ovary is also pubescent.

FRUIT

Maturity when described: Ripe for commercial harvesting and shipment approximately June 18 through June 26 under the ecological conditions prevailing in the San Joaquin Valley of central California.

Size:

*Uniformity.*—Uniform. The size of the instant variety is considered large for the species.

*Average cheek diameter.*—Approximately 72 mm.

*Average suture diameter.*—Approximately 73 mm.

*Average axial diameter.*—Approximately 70 mm.

Form:

*Uniformity.*—Uniform, and slightly asymmetrical.

*Shape.*—Nearly round in its axial aspect and broadly ovate and occasionally slightly oblate in its lateral aspect.

Suture:

*Generally.*—A moderately wide and distinct suture line extends from the base to the apex. A moderate amount of stitching may be evident along the entire length of the suture line. The suture color, as a general matter, appears lighter than the surrounding skin color and often assumes the ground color of the fruit. The surface texture of the suture is considered to be moderately rough and some calloused tissue may be evident from time to time. A distinct depression is evident along the ventral suture and is disposed in close proximity to the apex.

Ventral surface:

*Generally.*—Variable. The ventral surface appears rounded and occasionally moderately protruding. A moderate amount of lipping is also present. The sides are usually unequal but may at occasions appear only slightly so.

Stem cavity:

*Generally.*—Small.

*Average length.*—Approximately 29–32 mm.

*Average width.*—Approximately 26–30 mm.

*Average depth.*—Approximately 10–12 mm.

*Form.*—Generally — Oval. Further, the ventral suture line usually appears deeply folded inside the stem cavity.

Base:

*Shape.*—Rounded and occasionally slightly truncate. The fruit base will normally be positioned at approximately right angles to the fruit axis. Variable. The base may appear rounded although occasionally it may appear slightly pointed. The pistil point is also variable, that is it may be located in a perfectly apical position or may occasionally be disposed in a slightly oblique position. Further a distinct depression is evident on both the ventral and dorsal suture sides of the apex in close proximity to the pistil point.

Stem:

*Generally.*—Moderately short as compared with other varieties.

*Average length.*—Approximately 7–9 mm.

*Average thickness.*—Approximately 4 mm.

*Color.*—Pale green, (19-J-3).

Skin:

*Thickness.*—Average.

*Flavor.*—Mild.

*Tendency to crack.*—Not observed.

*Tenacious to flesh.*—Yes, however the skin will readily peel away from the flesh with advancing maturity.

*Pubescence.*—Present, however it is light and very short.

*Color.*—Blush — Variable, approximately 20% to 50% of the blush is a dark garnet red, (7-J-9) which shades into a light orange-red, (5-J-10) of varying percentages. Further the blush color may cover approximately 30% to 80% of the entire surface of the fruit. A moderate number of white dots may be present and are located over the apical shoulder area and occasionally around the apex.

*Flesh color.*—Generally — At commercial maturity the flesh color is a substantially uniform yellow which extends from the skin to the pit cavity, (10-H-6).

*Pit cavity.*—Color — Stained a dark red, (4-K-10). This red coloration may occasionally extend from the pit cavity into the flesh a distance of approximately 5–10 mm. A small amount of red flecking may appear in the flesh from time to time.

*Ground color.*—Yellow-gold, (10-J-6).

*Flesh texture.*—Generally — Firm and crisp at commercial maturity and becoming melting with advancing maturity.

*Flesh fibers.*—Numbers — Numerous. Color — Light yellow. These fibers are most readily evident in the immediate vicinity of the pit cavity. Average length — Medium. Texture — Tender.

Ripening:

*Generally.*—Even.

*Flavor.*—Good, however it is slightly acidic.

*Eating quality.*—Above average.

Stone:

*Attachment.*—Generally considered freestone. The stone is held tightly in the pit cavity, and there is usually no air space present. The stone may appear to cling slightly to the flesh along both the ventral and dorsal sutures.

*Size.*—Generally — Medium.

*Average length.*—Approximately 34 mm.

*Average width.*—Approximately 23 mm.

*Average thickness.*—Approximately 18 mm.

*Fibers.*—Generally — Few in number and considered moderately short.

*Form.*—Generally — Irregular, but appearing roughly oval.

*Base.*—Form — Broadly truncate. The base angle appears oblique to the stone axis and also appears shorter on the ventral suture side.

*Hilum.*—Shape — Narrow and heavily eroded. It also appears roughly oval in form.

*Apex.*—Shape — Acute, and appearing both thin and quite sharp.

*Stone sides.*—Shape — Substantially equal. Further, the stone surface is moderately rough with some fine grooves appearing over the basal shoulder areas. Deeper grooves and ridges occur in the vicinity of the apical shoulders. Numerous irregular pits are evident over the lateral surfaces.

*Ventral edge.*—Shape — Moderately broad and having low wings extending from the base to the apex. The wings converge apically.

*Dorsal edge.*—Generally — A deep and wide groove is evident from the base to just above midstone. That portion of the apical shoulder along the dorsal edge appears to be heavily eroded and nearly concave in shape.

*Color.*—Generally — Light brown, (12-F-5). The stone surface is usually stained with red.

*Tendency to split.*—Not observed.

Fruit use: The subject variety "Fancy Lady" is a fresh market peach for both local and long distance shipping.

Keeping quality: Good.

Storage quality: The variety has not been shipped in volume, however the firm and crisp texture of the fruit as well as the tenacious nature of the skin at commercial maturity strongly indicates that this variety will have noteworthy shipping characteristics.

Although the new variety of peach tree possesses the described characteristics as a result of the growing conditions prevailing in Reedley, Calif., in the central part of the San Joaquin Valley, it is to be understood that variations of the usual magnitude and characteristics incident to growing conditions, fertilization, pruning and pest control are to be expected.

Having thus described and illustrated our new variety of peach tree, what is new and desired to be secured by Letters Patent is:

1. A new and distinct variety of peach tree substantially as illustrated and described and which is somewhat similar to the Sparkle Peach Tree (U.S. Plant Pat. No. 3,298) from which it was discovered as a scaffold mutation, but from which it is distinguished therefrom and characterized principally as to novelty by bearing fruit which are mature for commercial harvesting and shipment approximately June 18 through June 26, the date of harvesting being approximately one month earlier than the Sparkle Peach Tree and which further produces fruit which have a more symmetrical shape and which are more highly colored than the fruit produced by the Sparkle Peach Tree.

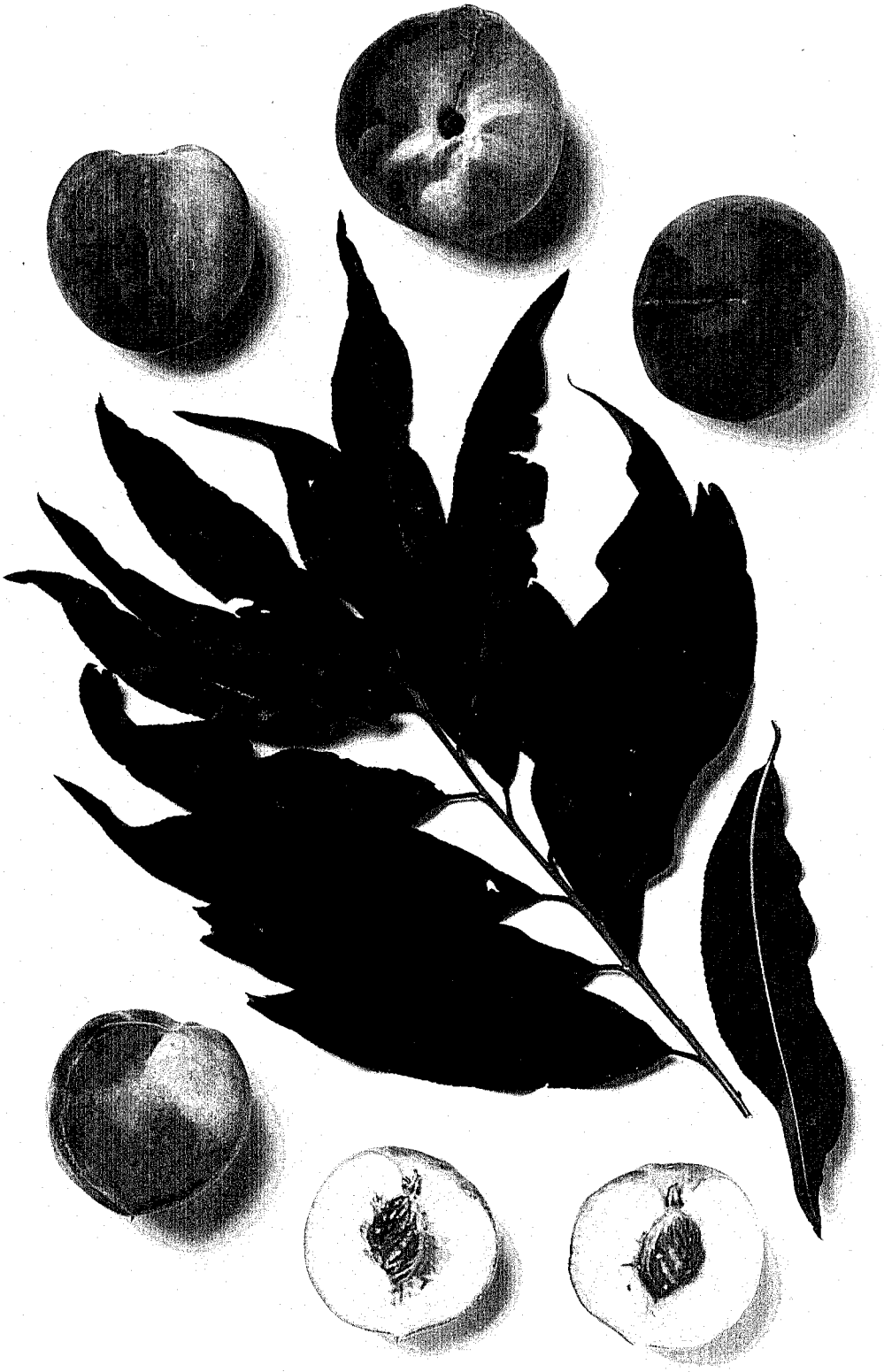

* * * * *